United States Patent [19]

Murillo Araujo et al.

[11] 4,318,987
[45] Mar. 9, 1982

[54] β-CAROTENE PRODUCING STRAINS OF THE FUNGUS PHYCOMYCES BLAKESLEENUS

[76] Inventors: Francisco J. Murillo Araujo, C/Turdetania, 3-1°C; Isabel López Calderon, C/Virgen de la Antigua, 20, 1°A; Isabel Lopez Díaz, C/Gerona, 21, 3°A; Enrique Cerdá Olmedo, C/Avd. Reina Mercedes, 27, 6°D, all of Sevilla, Spain

[21] Appl. No.: 94,923

[22] Filed: Nov. 16, 1979

[51] Int. Cl.³ .................. C12N 15/00; C12P 23/00; C12N 1/14; C12R 1/645
[52] U.S. Cl. .................................. 435/172; 435/67; 435/254; 435/911
[58] Field of Search .............. 435/172, 67, 911, 254

[56] References Cited

U.S. PATENT DOCUMENTS

| | | | |
|---|---|---|---|
| 2,820,742 | 1/1958 | Pontecorvo et al. | 435/172 |
| 2,890,989 | 6/1959 | Anderson | 435/254 |
| 3,330,737 | 7/1967 | Marnati et al. | 435/67 |
| 3,579,424 | 5/1971 | Purcell et al. | 435/67 |

OTHER PUBLICATIONS

Murillo et al., "Regulation of Carotene Synthesis in Phycomyces", *Molec. gen. Genet.*, vol. 148, (1976), pp. 19-24.
Cerda-Olmedo et al., "Genetic Classification of the Lethal Effects of Various Agents on Heterokaryotic Spores of Phycomyces", *Mutation Res.*, vol. 9, (1970), pp. 369-384.
Ootaki, "A New Method for Heterokaryons Formation in Phycomyces", *Molec. gen. Genet.*, vol. 121, (1973), pp. 49-56.
Heisenberg et al., "Segregation of Heterokaryons in the Asexual Cycle of Phycomyces", *Molec. Gen. Genetics*, vol. 102, (1968), pp. 187-195.
Righelato, "Growth Kinetics of Mycelial Fungi", *The Filamentous Fungi*, vol. 1, Smith et al. ed., Edward Arnold Ltd., London, (1975), pp. 116, 117.
Goodwin, Carotenoids", *The Filamentous Fungi*, vol. II, Smith et al. ed., Edward Arnold Ltd., London, (1976), pp. 423-444.
Ende, "Sexual Morphogensis in the Phycomycetes", *The Filamentous Fungi*, vol. III, Smith et al. ed., Edward Arnold Ltd., London, (1976), pp. 257-274.

Primary Examiner—Thomas Wiseman
Attorney, Agent, or Firm—Wenderoth, Lind & Ponack

[57] ABSTRACT

This invention refers to the obtention of strains of the fungus Phycomyces blakesleeanus accumulated by the β-carotene pigments in amounts which permit the use of these strains in the production on an industrial scale of said pigment. By genetic manipulations, strains simultaneously and constitutively incorporating various stimulating effects have been isolated. The resulting strains produce β-carotene in a proportion of approximately 2.5% of its dry weight, which constitutes almost 1000 times more than that which the natural microorganism would produce under the same conditions. This production level, together with the simplicity in cultivating and manipulating same, makes them interesting in the development of an industrial process for producing β-carotene by fermentation. The β-carotene produced by fermentation, besides its low cost, would have the advantage of not being contaminated with the reagents and catalysts used in the organic synthesis.

2 Claims, No Drawings

β-CAROTENE PRODUCING STRAINS OF THE FUNGUS PHYCOMYCES BLAKESLEENUS

BACKGROUND OF THE INVENTION

The production of β-carotene by the fungus *Phycomyces blakesleeanus* depends on the culture media and conditions but it is generally small. In the dark, this fungus produces about 50 micrograms of the pigment per gram of dry material (μg/g dry weight), an amount inappropriate for the desired object.

Various ways of increasing this production are known. One of them consists in the addition of vitamin A to the normal culture medium of this organism. This addition causes the accumulation of up to 2,000 μg/g dry weight of β-carotene, but the required concentrations of the vitamin are prohibitively high. Amounts up to 2,000 μg/g dry weight have been observed under the best conditions in the presence of β-ionone.

Another way of increasing the production of β-carotene already described, is the formation of the strains containing nuclei of the two known wild sexual types of Phycomyces, which are represented by the symbols (+) and (−). The method for obtaining this type of strain, denominated intersexual heterokaryon, has been described. These strains accumulate up to 500 μg/g dry weight of β-carotene, they have a peculiar morphology, with formation of small hyphae areas, or pseudophores, and they are unstable: they tend to segregate the components homokaryotically.

In the Mucorales, the interaction between the mycelia of opposite sex leads to a greater carotenogenes is through the formation of trisporic acids. The cultures mixed with strains of *Blakeslea trispora* of opposite sex in the presence of β-ionone, have been considered as promising for the production of β-carotene. However, it is difficult to maintain the appropriate sex relations in large cultures.

It is also known that the production of β-carotene of the wild type is controlled by the gene carS and that strains genetically altered by mutation in said gene produce up to 4000 μg/g dry weight of β-carotene. Two of the known strains of this type are the strain C115 obtained from a wild strain having a (−) sex, and the strain M1 obtained from a wild strain having a (+) sex. The carS mutants are still sensitive to vitamin A, but a double mutant, strain S106, has been obtained which reaches 6000 μg/g dry weight. The new mutation, car-102 makes the S106 insensitive to vitamin A. The stimulating canal activated by vitamin A has thus been converted as constitutive of this strain.

It is known that the three mentioned types of stimulations, presence of vitamin A, position of intersexuality, and alteration of the gene carS, act independently from one another.

SUMMARY OF THE INVENTION

The object of this invention is the obtention of strains of the fungus *Phycomyces blakesleeanus* accumulated by the μ-carotene pigment in an amount which permits the use of these strains in the production, on an industrial scale, of said pigment.

The technique which we describe presents the novelty of combining in a single strain the three types of stimulations previously mentioned, furthermore making unnecessary the addition of vitamin A to the culture medium to cause the stimulation due to said vitamin.

Presently four similar strains have been obtained, which are denominated, respectively:
S218 * S219
S242 * S243
S244 * S245
S246 * S247.

The first of the mentioned strains was the origin of the other three and the characteristics thereof are described herebelow. The three derived strains have the same characteristics, with the exception that the colour thereof is more uniform and the growth thereof is slower.

Description of strain S218 * S219

The general characteristics thereof are those of the strain *Phycomyces blakesleeanus* Bgff., to which it pertains.

The colour of the mycelium and sporangiophores is a very intense orange-red, not completely uniform but, at first sight, intensity shadings, and under a microscope, intracellular accumulations of pigments through the hyphae can be seen. The main pigment is the β-carotene, present in the amounts described in the specification.

The growth of the mycelium is somewhat slower than in normal strains of this species, it takes almost 5 days (instead of 3) to completely cover the surface of the 10 cm. Petri plate, under the normal media and temperature conditions. The dry weight of mycelium per Petri plate is greater than in normal strains, due to a considerable thickening of the mycelium layer.

In solid media, the surface of the mycelium presents various pseudophores, as corresponds to the presence of genetic determiing factors of both sexes (+) and (−) in the same mycelium.

It does not present sexual reaction against the strains *Phycomyces blakesleeanus* of (+) and (−) sexes.

It produces very few sporangiophores and never as early as the normal strains (3 or 4 days). The production of sporangiophores, although very scarce, improves after more prolonged incubations (about 2 weeks) in uncovered Petriplates and under intense illumination.

The two components present in this strain do not segregate out homokaryotically by mycelium growth nor by reproduction through spores. Both the transplants of mycelia fragments as well as the spores produce mycelia having the characteristics of the described strain.

MATERIALS AND METHODS

The strains of *Phycomyces blakesleeanus* used in this work are reflected in Table I. The two heterokaryotic components are separated by an asterisk.

For all the quantitative studies, the cultures are developed on a minimum solid medium at 22° C. for 4 days. In a few cases the cultures were developed on potato-dextrose agar since the low cost thereof can be an advantage in large scale applications. To observe the different colonies, the minimum medium was supplemented with 1 mg. of yeast extract per milliliter and acidulated at a pH of 3.3. The detailed obtention of these media has been previously described (M. Heisenberg and E. Cerdá Olmedo, *Molecular and General Genetics* vol. 102, p. 187–195, 1968).

The extraction of carotenes and the chromatographic separation and identification thereof have previously been described.

The mutants were isolated after having been treated with 100 μg of N-methyl-N'-nitro-N-nitrosoguanidine NTG per milliliter, in a citrate-phosphate buffer at a pH of 7, as previously described (E. Cerda Olmedo and P. Reau, *Mutation Research*, vol. 9, p. 369–384, 1970).

The first step in the preparation of the mentioned strains consisted in obtaining, from the strain C115, proceeding from the cultures collection of the Technological Institute of California, a strain which could reach production levels of β-carotene of the strain C115 when cultivated in the presence of vitamin A, but without having to add this vitamin. To obtain this strain, spores of C115 were untagenized with NTG and, among the survivor spores, any giving a more intense colouring than that shown by C115 was searched for. Said strain is that denominated S106 which accumulates about 6000 μg/g dry weight of β-carotene, both in the presence and in the absence of vitamin A and about whose isolement we have written in detail in a prior publication (F. J. Murillo and E. Cerdá Olmedo, *Molecular and General Genetics*, vol. 148, p. 19–24, 1976).

The second step consisted in the construction of the intersexual heterokaryon which contained nuclei of the strains S106 and M1, which we denominated S106 M1, and which produces from 14,000 to 25,000 μg/g dry weight of β-carotene. The process for obtaining heterokaryons between any of two strains of Phycomyces has been previously published (T. Ootaki, *Molecular and General Genetics*, vol. 121, p. 49–56, 1973).

The maintenance and propagation of an intersexual strain presents many difficulties, since sectors having a single sexual type frequently appear in the culture thereof. This behaviour reduces the yield of the production of β-carotene. On the other hand, the easiest way of initiating new cultures of Phycomyces is by innoculating the spores forming this organism. It is known that these spores contain a variable but small number of nuclei, from 1 to 7, and that a high proportion of the spores produced by an intersexual strain contains a single nucleus or various nuclei of the same sexual type and, therefore, they have lost the intersexual character.

One way of solving this problem resides in that the two types of nuclei of the intersexual strain should contain a type of genetic alteration known as "recessive lethal" mutation. This mutation, since it affects a gene which controls a vital function of the organism, prevents same from surviving, unless it also contains nuclei not altered in said gene which guarantee the normal appearance of the corresponding function. The following step of our process has been the introduction of recessive lethal mutations in each one of the two types of nuclei of the strain S106 M1, so that the genes affected in the nuclei of the type S106 control functions differing from those affected in the nuclei of type M1. The method consisted in treating the mycelia spores S106 * M1 with NTG up to a survival level of approximately 0.1%, according to a process previously described in detail (E. Cerda Olmedo and P. Rean, *Mutation Research*, vol. 9, p. 369–384, 1970). The majority of the nuclei are thus inactivated and the majority of the survivors are homokaryotic. Among the heterokaryotic survivors, there are many which cannot segregate any of the components homokaryotically, due to the introduction of recessive lethal mutations. In a total of 117 survivors of the treatment, taken from the most brilliantly coloured, segregation was determined by depositing the spores thereof on an acid medium (M. Heisenberg and E. Cerdá Olmedo, *Molecular and General Genetics*, vol. 102, p. 187–195, 1968). The heterokaryons S218 * S219 and S242 * S243 were thus obtained. They produce considerable amounts of β-carotene (Table II) and no homokaryon is found among their progeny, although they still present a wide range of nuclear relations, leading to variations in the β-carotene content.

The variation in nuclear relations could be limited if the lethal mutations were not totally recessive. If both components of the heterokaryon contain mutations, or series of mutations, therefore, not facilitating mycelia with more than 70% of the corresponding nuclei, the nuclear proportions should be limited to the range of 30–70%. The spores of the heterokaryons S218 * S219 were treated with NTG in the same way described by E. Cerdá Olmedo and P. Reau (prior reference) and a search for the stable strains led to the isolation of S244 * S245 and S246 S247. These heterokaryons are apparently very uniform and present a high β-carotene content.

The four strains described produce up to 25,000 μg/g dry weight of β-carotene. In cultures of these intersexual strains there are no sectors having a single type of nucleus, since it would be inviable and, therefore, the stimulation of the production of β-carotene by intersexuality is maintained uniform throughout the culture. On the other hand, of the spores produced by this strain only those containing the two sexual types of nuclei give rise to growth, since those having a single nucleus or various nuclei of the same type are inviable. Therefore, the problems of initiating new intersexual cultures from these spores have been avoided.

TABLE I

Strains of *Phycomyces blakesleeanus* used in the invention

| Strain | Genotype | Main carotenoid accumulated (ug/g dry weight) |
|---|---|---|
| NRRL 1554 | Wild type (+) | β-carotene (56) |
| M1 | CarS43 (+) | β-carotene (4160) |
| S106 | CarS42 car-102 mad-103 (−) | β-carotene (5595) |

TABLE II

Production of β-carotene in intersexual heterokaryons S106 * M1, and derivatives thereof

| Strain | β-carotene(ug/g dry weight) |
|---|---|
| S106 * M1, *mycelium* A | 14,340 |
| S106 * M1, *mycelium* B | 18,450 |
| S106 * M1, *mycelium* C | 20,325 |
| S106 * M1, *mycelium* D | 20,500 |
| S106 * M1, *mycelium* E | 25,342 |
| S219 * S219 | 16,000 (12,620)* |
| S242 * S243 | 15,600 (9000) |
| S244 * S245 | 19,120 (14,120) |
| S246 * S247 | 13,470 (25,230) |

*The numbers in parenthesis correspond to cultures in potato-dextrose agar.

In our opinion, the production of β-carotene in the four mentioned strains is the maximum reached by any known organism. Said production should permit the use of these strains in the obtention, on an industrial scale, of β-carotene under such profitable conditions which favourably compete with the methods of artificial chemical synthesis used at present. In the past, there were no biological processes for obtaining -carotene which could compete, with respect to profitability, with such synthetic methods. The maximum production of other organisms does not reach that of our strains and furthermore it requires special cultivation conditions (illumination, additives to the culture medium, etc.) which increase the costs of production. Such requirements are not necessary in our case.

The strains S218 * S219, S242 * S243, S244 * S245 and S246 * S247 have been deposited in the Public Depository and Strain Collection of the Faculty of Biology in the University of Sevilla, Sevilla, Spain.

The aforementioned strains have the following characteristics:

S218 * S219: General characteristics are the same as those of the species *Phycomyces blakesleeanus* Bgff., to which it pertains;

Colour of the mycelium and sporangiophores of said S218 * S219: A very intense orange-red, not completely uniform but with intensity shadings at first sight and, under a microscope, intracellular accumulations of pigments can be seen throughout the hyphae; the main pigment of which is β-carotene;

Growth of the mycelium of said S218 * S219: somewhat slower than in normal strains of this species; and in solid media, the surface of the mycelium presents numerous pseudophores, as corresponds to the presence of genetic determinating factors of both sexes (+) and (−) in the same mycelium;

Sexual reaction of said S218 * S219 against strains of *Phycomyces blakesleeanus* of (+) and (−) sexes: negative;

Production of sporangiophores of said S218 * S219: very scarce and slower than in normal strains. The production of sporangiophores improves after prolonged incubations (about 2 weeks) in uncovered Petri plates and under intense illumination;

The two components present in the S218 * S219 strain do not segregate homokaryotically by mycelium growth nor by reproduction through spores and both the transplants of mycelia fragments as well as spores produce mycelia having the characteristics of the described strain;

Strains S242 * S243, S244 * S245, and S246 * S247 have characteristics like that of strain S218 * S219, with the exception that the colour thereof is more uniform and the growth thereof is slower.

We claim

1. A biologically pure strain of *Phycomyces blakesleeanus* capable of producing β-carotene selected from the group consisting of:
   S218 * S219,
   S242 * S243,
   S244 * S245, and
   S246 * S247
said strains having been deposited in the Public Depository and Strain Collection of the Faculty of Biology in the University of Sevilla, Sevilla, Spain.

2. In a process for the production of a biologically pure β-carotene producing strain of *Phycomyces blakesleeanus* described in claim 1, which comprises cultivating the fungus *Phycomyces blakesleeanus* in a suitable medium, isolating a strain denominated C115 therefrom, treating the spores of C115 with N-methyl-N'-nitro-N-nitrosoguanidine (NTG) in a suitable cultivating medium; isolating a strain denominated S106 and a strain M1 therefrom; and constructing an intersexual heterokaryon from the strains of S106 and M1 to obtain the strain S106 * M1; the latter strain of which contains nuclei of the former strains, all of said strains having been deposited in the Public Depository and Strain Collection of the Faculty of Biology in the University of Sevilla, Sevilla, Spain, the improvement which comprises:

(a) introducing recessive lethal mutations in each one of the types of nuclei of the strain S106 * M1 by treating the spores of mycelia S106 * M1 with N-methyl-N'-nitro-N-nitrosoguanidine (NTG) to a survival level of approximately 0.1% and isolating the heterokaryons S218 * S219 and S242 * S243 therefrom; and (b) treating the heterokaryons S218 * S219 with N-methyl-N'-nitro-N-nitrosoguanidine (NTG) and isolating the stable strains S244 * S245 and S246 * S247 therefrom.

* * * * *